United States Patent [19]
Askanazi et al.

[11] Patent Number: 5,278,190
[45] Date of Patent: Jan. 11, 1994

[54] METHOD FOR IMPROVING THE QUALITY OF SLEEP AND TREATING SLEEP DISORDERS

[75] Inventors: Jeffrey Askanazi, Haworth, N.J.; Susan Trimbo, Evanston, Ill.

[73] Assignee: Clintec Nutrition Co., Deerfield, Ill.

[21] Appl. No.: 865,464

[22] Filed: Apr. 9, 1992

Related U.S. Application Data

[63] Continuation-in-part of Ser. No. 582,527, Sep. 14, 1990, which is a continuation-in-part of Ser. No. 443,765, Nov. 30, 1989, Pat. No. 5,017,616.

[51] Int. Cl.$^5$ .............................. A61K 31/195
[52] U.S. Cl. .................... 514/561; 514/923
[58] Field of Search ................ 514/923, 561

[56] References Cited

U.S. PATENT DOCUMENTS

| | | | |
|---|---|---|---|
| 4,209,531 | 6/1980 | Berry | 514/561 |
| 4,298,601 | 11/1981 | Howard | 424/692 |
| 4,638,013 | 1/1987 | Moja et al. | 514/561 |
| 4,767,785 | 8/1988 | Georgieff | 514/561 |
| 5,006,559 | 4/1991 | Askanazi et al. | 514/561 |
| 5,017,616 | 5/1991 | Askanazi | 514/561 |

FOREIGN PATENT DOCUMENTS

| | | |
|---|---|---|
| 0144051 | 6/1985 | European Pat. Off. |
| 0434989 | 7/1991 | European Pat. Off. |
| 0499463 | 8/1992 | European Pat. Off. |
| 2037161 | 7/1980 | United Kingdom |

OTHER PUBLICATIONS

Manner et al., "Branched-Chain Amino Acids and Respiration", Nutrition, vol. 8, No. 5, 1992, pp. 311–315.
Kimmel et al., "Sleep Apnea Syndrome in Chronic Renal Disease", Am. J. Med. vol. 86, 1989, pp. 308–314.
Takala et al., "Changes in Respiratory Control Induced by Aminoacids", Critical Care Med., vol. 16, No. 5, 1988, pp. 465–469.
E. Soreide et al., Branched-Chain Amino Acid in Chronic Renal Failure Patients Respiratory and Sleep Effects, Kidney International, vol. 40 (1991), pp. 539–543.
Pharmacology of Benzodiazepines, (1982), pp. 187–236.
Roet Liste, (1987) p. 56.
Soltesz et al., Blood Glucose and Plasma Amino Acid Concentrations in Infants of Diabetic Mothers, Acta Paediatrics, vol. 61, No. 1, Jan. 1978, pp. 77–82.
Schultz et al., The Effect of Birth Asphyxia on Plasma Free Amino Acids in Prerterm Newborn Infants, Acta Paediatrica Academiae Scientiarum Hungarica, vol. 18 (2), pp. 123–130 (1977).
C. Weissman et al., Amino Acids and Respiration, Annals of Internal Medicine, vol. 98, No. 1, Jan. 1983, pp. 41–44.
J. Takala et al., Changes in Respiratory Control Induced by Amino Acid Infusions, Critical Care Medicine, vol. 16, No. 5, May 1988, pp. 465–469.
J. Askanazi et al., Effect of Protein Intake on Ventilatory Drive, Anesthesiology, vol. 60, No. 2, Feb. 1984, pp. 106–110.
A. Fein et al., Reversal of Sleep Apnea in Uremia by Dialysis, Arch Intern Med, vol. 147, Jul. 1987, pp. 1355–1356.
R. Millman et al., Sleep Apnea in Hemodialysis Patents: The Lack of Testosterone Effect on its Pathogenesis, Nephron 40: 407–410 (1985).
P. Kimmel et al., Sleep Apnea Syndrome in Chronic Renal Disease, The American Journal of MEdicine, vol. 86, Mar. 1989, pp. 308–314.
D. Prezant, Effect of Uremia and its Treatment of Pulmonary Function, Lung (1990) 168:1–14.
R. Evans et al., The Quality of Life of Patients with End-Stage Renal Disease, The New England Journal of Medicine, vol. 312, No. 9, Feb. 28, 1085, pp. 553–559.

Primary Examiner—Frederick E. Waddell
Assistant Examiner—Raymond J. Henley, III
Attorney, Agent, or Firm—Hill, Steadman & Simpson

[57] ABSTRACT

A method for improving the quality of sleep in a chronic renal failure patient is provided. To this end, the present invention provides a method of using branched-chain amino acids as an effective therapy for improving the quality of sleep. The branched-chain amino acid composition can be administered either parenterally or enterally, and can be administered alone or in combination with other nutrients. The composition can be administered during dialysis, intradialytic.

17 Claims, 1 Drawing Sheet

METHOD FOR IMPROVING THE QUALITY OF SLEEP AND TREATING SLEEP DISORDERS

BACKGROUND OF THE INVENTION

This is a continuation-in-part of U.S. patent application Ser. No. 07/582,527, filed on Sep. 14, 1990, pending that is a continuation-in-part of U.S. patent application Ser. No. 07/443,765 filed on Nov. 30, 1989, now U.S. Pat. No. 5,017,616.

The present invention relates to a method for the use of branched-chain amino acids to treat sleep disorders. More specifically, the present invention relates to a method for improving sleep quality in a chronic renal failure patient.

Sleep disorders may take the form of an abnormal pattern of sleep and increased requirements for medication as well as an overt sleep apnea.

Sleep apnea is recognized as a serious and often life threatening abnormality of the breathing pattern. See, Kales, et al, *Sleep Disorders: Sleep Apneas and Narcolepsy*, Ann. Intern. Med., 106:434-443, 1987. The morbidity of sleep apnea is due to a decrease oxygenation of the arterial blood and carbon dioxide retention secondarily to alveolar hypoventilation.

The condition of sleep apnea has been defined as the cessation of breathing for at least 10 seconds, that occurs at least 30 times during a 7 hour period of sleep. This definition, however, is based on sleep laboratory studies and accordingly, is not clinically applicable. Instead, arterial oxygen desaturation during sleep is the critical factor in determining sleep apnea. See, Block, et al, *Sleep Apnea, Hypopnea and Oxygen Desaturation in Normal Subjects*, New England Journal of Medicine, 300:513-517, 1979.

The sleep apnea syndrome has been observed as a primary disease in otherwise healthy subjects. Apneas can be divided into three sub-groups: central; obstructive; and mixed. Abnormal respiratory control is believed to be involved in all types of sleep apneas. Apneic breathing patterns during sleep occur also in association with certain other conditions, such as: morbid obesity; coronary disease; and congestive heart failure. See, Walse, et al, *Upper Airway Obstruction in Obese Patients With Sleep Disturbances and Somnolence*, Ann. Intern. Med. 76: 185-192, 1972; DeOlazabal, et al, *Disordered Breathing and Hypoxia During Sleep in Coronary Artery Disease*, Chest, 82:548-552, 1982; and Dark, et al, *Breathing Pattern Abnormalities and Arterial Desaturation During Sleep in the Congestive Heart Failure Syndrome, Improvement Following Medical Therapy*, Chest, 91:833-836, 1987. Patients recovering from anesthesia also frequently exhibit apneic breathing patterns.

Most patients with sleep apnea snore heavily and many exhibit severe oxygen desaturation. Oxygen desaturation during sleep may be associated with pulmonary and systematic hypertension and cardiac arrhythmias. Tilkian, et al, Sleep-Induced Apnea Syndrome, *Prevalence of Cardiac Arrhythmias and Their Reversal After Tracheostomy*, Am.J.Med. 63(3):348-358, 1976: and Tilkian, et al, *Hemodynamics in Sleep-Induced Apnea*, Am. Intern. Med. 85(6):714-719, 1977.

The typical management of sleep apnea syndrome is to relieve upper air obstruction and to also stimulate respiratory activity. Typically, pharmacologic techniques are utilized to achieve these goals. However, drug therapy alone is not usually effective in relieving sleep apneas. Moreover, such drug therapies are often associated with adverse side effects.

One drug that is used is Medroxyuprogesterone acetate (MPA). MPA has been found to be a moderate, sustained ventilatory stimulant in man. MPA reduces sleep apnea in less than half of all patients. Strohl, et al, *Progesterone Administration and Progressive Sleep Apneas*, J.A.M.A., 245:1230-1232, 1981. But, MPA causes impotence in men and therefore the desirability and use of this drug is limited.

Another drug, protiptyline has been found to improve sleep apnea in some patients. This drug, however, is associated with such serious side effects such as: constipation; urinary retention; ataxia; and confusion. Brownell, et al, *Protiptyline in Obstructive Sleep Apnea*, New England Journal of Medicine, 307:1037-1042, 1982.

Accordingly, although pharmacologic interventions can be, in some cases, effective in decreasing the frequency and duration of sleep apneas, and the extent of oxygen desaturation in patients, the usefulness of such drug therapy is limited due to the adverse side effects of such drugs. Therefore, there is a need for an improved therapy for treating patients with sleep apnea.

Sleep apnea has also become of increasing clinical interest in chronic renal failure patients. See: Millman et al, *Sleep Apnea in Hemodialysis Patients: The Lack of Testerone Effect On Its Pathogenesis*, Nephron 1985:40:407-10; Fein et al, *Reversal of Sleep Apnea In Uremia by Dialysis*, Arch. Internal Med. 1987:147:1355-56; and Kimmel et al, *Sleep Apnea Syndrome In Chronic Renal Disease*, Am. J. Med. 1989:86:308-14.

In chronic renal patients, two separate forms of sleep apnea occur: a) obstructive apnea (wherein there is no airflow but respiratory effort); and b) central apnea (wherein there is no airflow and no respiratory effort). The detrimental clinical effects of sleep apnea can include arterial oxygen desaturation, cardiac arrhythmias, and pulmonary and systemic hypertension. The results of sleep apnea extend to the awake state and include excessive day-time sleepiness, mood and personality disorders as well as impaired intellectual function.

Improvements in both physiology and symptomology have been reported with different pharmacological agents. See Parish, et al, *Cardiovascular Effects of Sleep Disorders*, Chest 1990:97:1220-26; NHLBI Workshop Summary, *Respiratory Disorders of Sleep, Pathophysiology, Clinical Implications and Therapeutic Approaches*, Am Rev. Respir. Dis. 1987:136:755-61; and Douglas et al, *Breathing During Sleep In Patients With Obstructive Lung Disease*, Am. Rev. Respir. Dis. 1990:141:1055-70. However, common side effects such as peripheral neuropathy, paresthesia, acidosis, impotence, and dry mouth have limited the long-term application of these agents. Additionally, pharmacological intervention typically worsens the quality of the patient's sleep.

Abnormalities of sleep pattern with reduced sleep quality are common in chronic renal failure patients whether or not they also experience apnea of renal failure. Indeed, renal patients on hemodialysis have a 60% to 80% incidence of sleep disturbances. Poorer quality of sleep is expressed in chronic renal failure patients by less time spent in sleep, increased time to fall asleep, and less REM sleep.

The effects of an abnormal sleep pattern, or reduced quality of sleep, results in daytime drowsiness and fatigue which can limit functional capacity. Mood and personality disorders as well as impaired intellectual functioning may result.

In an attempt to improve the quality of sleep, many chronic renal failure patients resort to sedatives and tranquilizers. Benzodiazepines are widely used in this regard for their tranquilizing and sedative effects. Benzodiazepines include: diazepam, nitrazepam, flurazepam, lorazepam, chlordiazepoxide, and midazolam. Unfortunately, sedatives are not without their side effects including daytime sleepiness and reduced daytime alertness. See, for example, William Dement et al, "Changes in daytime sleepiness/alertness with nighttime benzodiazepines," Pharmacology of Benzodiazepines, proceedings of a conference held in the Masur Auditorium, National Institute of Health, Bethesda, Md. on Apr. 12-14, 1982.

With respect to chronic renal failure patients who may suffer apnea, benzodiazepines as a sedative provided additional concerns in addition to daytime sleepiness and reduced daytime alertness. Reports have associated benzodiazepines with precipitating respiratory failure in patients with pre-existing pulmonary diseases. See, Clark et al, "Respiratory Depression Caused by Nitrazepam in Patients with Respiratory Failure," Lancet 2:737-738 (1971); Pines, "Nitrazepam in Chronic Obstructive Bronchitis," Brit. Med. J. 3:352 (1972); and Model et al, "Effects of Chlordiazepoxide in Respiratory Failure Due to Chronic Bronchitis," Lancet 2:869-870 (1973). Indeed, Guilleminault et al, "Benzodiazepines and Respiration During Sleep," Pharmacology of Benzodiazepines (1982) states:

... Our results make it clear that the effects of BZ on breathing are not simple. If a subject presents a significant breathing problem before drug administration, BZ may worsen it, but the type of defect may significantly influence the impact of the drug. For example, it appears that subjects with moderately severe obstructive sleep apnea syndrome may easily be made worse by BZ intake at bedtime. Similarly, patients with obesity-hypoventilation syndrome or moderate COPD and a past history of acute respiratory failure with, for example, upper respiratory infection, may present a worsening of their problem with one dosage of BZ. But this effect was not consistent in all COPD patients. One patient with primary alveolar hypoventilation syndrome was not significantly worsened by the drug administration. Also, although BZ may increase the amount of apnea (essentially of the central type) associated with significant oxygen desaturation in elderly subjects, the findings are far from consistent.

There is therefore a need for a method of improving the quality of sleep in a chronic renal failure patient without using benzodiazepines.

SUMMARY OF THE INVENTION

The present invention provides a method for improving the quality of sleep. More specifically, the present invention provides a method for improving the quality of sleep in a chronic renal failure patient. To this end, the present invention provides a method of using branched-chain amino acids as an effective therapy for improving the quality of sleep. The branched-chain amino acid composition can be administered either parenterally or enterally, and can be administered alone or in combination with other nutrients. As used herein, parenteral includes, in addition to intravenous administration, administration through the peritoneum.

In an embodiment of the method of the present invention, the branched chain amino acids are given intradialytic.

In an embodiment, preferably, the branched-chain amino acids comprise 60 to 85% of an amino acid solution that is administered to the patient.

In an embodiment of the present invention, the composition comprises, per 100 ml, approximately 1.30 grams of isoleucine, 1.38 grams of leucine, and 1.24 grams of valine.

In an embodiment of the method of the present invention, approximately 4 grams of branched-chain amino acids are administered per hour.

Additional features and advantages of the present invention are described in, and will be apparent from, the detailed description of the presently preferred embodiments and the drawings.

DETAILED DESCRIPTION OF THE PRESENTLY PREFERRED EMBODIMENTS

Figure 1:
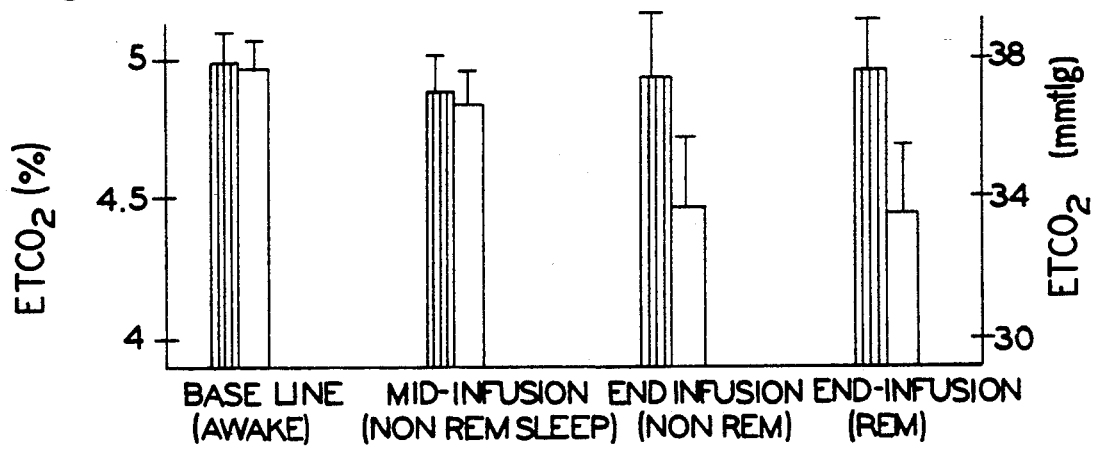
FIG. 1 illustrates, graphically, end-tidal ($EtCO_2$) during nocturnal infusion of a saline and a 4% branched-chain amino acid solution.

Branched-chain amino acid infusions have been shown to increase ventilatory drive when compared to conventional amino acid solutions and 5% dextrose. The infusion of amino acids increases ventilation by shifting the response curve of minute ventilation to arterial carbon dioxide tension to the left during carbon dioxide inhalation.

The inventors of the present invention have found that by altering an amino acid composition, by increasing the amount of branched-chain amino acids, an increase in ventilation and a decrease in arterial carbon dioxide tension is achieved. Branched-chain amino acids induce a larger decrease in arterial carbon dioxide tension and a larger increase in ventilatory response to carbon dioxide than a conventional amino acid solution. It has been found that branched-chain amino acids will induce a larger decrease in arterial carbon dioxide tension and a larger increase in ventilatory response to carbon dioxide than a conventional amino acid solution when infused for four hours after an overnight fast. This affect is even more dramatic when the infusion is continued over a 48 hour period.

The inventors of the present invention have also surprisingly found that the use of branched-chain amino acids improves sleep quality in chronic renal failure patients. The infusion of branched-chain amino acids significantly increased the percentage of REM sleep, length of sleep, and also tended to reduce the time before falling asleep.

Branched-chain amino acids therefore provide a method for improving the quality of sleep of chronic renal failure patients without the need for sedatives. The method of the present invention thereby allows a renal failure patient to reduce, or completely eliminate, the need for sleep aids such as benzodiazepines.

By way of example, and not limitation, examples of the present invention will now be set forth.

EXAMPLES

Example No. 1

Five non-smoking healthy male volunteers (24 to 32 years of age), with no sleep disorders and who were not taking any medication, were studied. The subjects were studied on three separate nights. One night was a control that did not include the infusion of any solution and on the other two nights a continuous infusion of either BCAA (3.5% solution of 100% BCAA) or placebo (½ normal saline) was administered. The composition of the BCAA solution used was as follows:

| Composition Of BCAA Solution (per 100 ml) | |
|---|---|
| Isoleucine | 1.38 g |
| Leucine | 1.38 g |
| Valine | 1.24 g |
| Total nitrogen | 443 mg |

The BCAAs/saline solutions were infused in a single blind crossover design with infusion/control nights randomly assigned within every patient. The patients were allowed no food intake after 5 pm and no stimulants (i.e., coffee) were allowed after 12 noon on the study days.

The subjects were admitted at 8:30 p.m. to a sleep-awake center. On the nights they were to receive an infusion, a peripheral cannula was inserted into the patients for the infusion. Sleep stages were studied using a 12-channel polysomnographic monitor (Grass P78). Chest wall movements were measured with a pneumograph consisting of a small circular rubber bellows attached around the chest. The bellows were connected to a volumetric pressure transducer. The signals were amplified with a DC amplifier. Air flow at the mouth and nose was measured by a thermistor placed at each nostril and the upper lip in the midline position. An ear oximeter (Ohmeda Biox 3700) was used to record oxy-hemoglobin saturation. End tidal $CO_2$ was measured using a capnograph (Normocap, Datex, Finland), the sampling tube was placed in the nasopharynx. A continuous electrocardiogram ran during the night.

The infusion solutions were started one hour prior to the estimated bedtime. The infusion rate was 100 ml/hour and infusion was discontinued in the morning at 7:30 a.m. The BCAA dose was 4 grams of amino acids/hour responding 0.443 grams of nitrogen/hour.

The end-tidal $CO_2$ levels during nights of BCAA infusion ($44\pm5$ mmHg) were lower than during control nights (C: $52\pm1$ mmHg, $p<0.01$ and S: $50\pm3$ mmHg, $p<0.05$). There was a trend ($p<0.2$) of increase in $O_2$-saturation levels. The results are set forth in Table 1 below:

TABLE 1

The highest end-tidal $CO_2$ (ETCO$_2$), and lowest SaO$_2$ values during the study nights; C (control nights without infusion), BCAA and NaCl

|  | C | BCAA | NaCl |
|---|---|---|---|
| ETCO$_2$ (mm Hg) | $52\pm1.4$ | $44\pm5.3$ | $50\pm2.6$ |
| SaO$_2$ (%) | $93\pm1.6$ | $95\pm2.3$ | $94\pm0.5$ |

There was no significant change in the amount of REM sleep. The amount of stage 3 sleep and the combined stage 3 & 4 sleep were greater during BCAA nights than control nights ($7.2\pm4.0\%$ vs $4.3\pm2.8\%$, $p<0.05$ and $15.9\pm3.0\%$ Vs. $12.3\pm3.9\%$, $p<0.02$, respectively). Sleep efficiency was slightly, but not significantly, decreased with either infusion (BCAA:$87\pm8$, NaCl:$87\pm8$, and C:$92\pm10$). One patient had 10 apneic episodes on the control night, 5 with NaCl, but none with BCAA infusion. The polysomnographic data is summarized in Table 2 below:

TABLE 2

The polysomnograph data from the three study nights

|  | C | BCAA | NaCl |
|---|---|---|---|
| Sleep efficiency | $92\pm10$ | $87\pm8$ | $87\pm8$ |
| Sleep latency | $2.1\pm3.2$ | $4.7\pm4.9$ | $2.1\pm1.5$ |
| Stage 1 sleep | $3.2\pm2.3$ | $5.3\pm5$ | $4.5\pm1.8$ |
| Stage 2 sleep | $59\pm3.7$ | $59\pm3.2$ | $62\pm5.5$ |
| Stage 3 sleep | $4.3\pm2.8$ | $7.2\pm4$ | $9\pm6$ |
| Stage 4 sleep | $8\pm6$ | $7\pm3$ | $6\pm5$ |
| Stage 3 & 4 | $12\pm4$ | $16\pm3$ | $15\pm9$ |
| REM sleep | $25\pm6$ | $20\pm5$ | $19\pm4$ |
| REM latency | $80\pm36$ | $95\pm109$ | $73\pm17$ |
| Apneas | $2.5\pm5$ | $0\pm0$ | $1.3\pm2.5$ |
| Hypopneas | $7\pm11$ | $4\pm6$ | $4\pm6$ |

All subjects had slightly hypercapnic highest end-tidal $CO_2$ values during both control nights and BCAA infusion decreased it to eucapnic levels (range 44-36 mmHg). BCAA infusions did not cause hypocapnia and thus the risks of causing hypoventilation and respiratory alkalosis appears negligible. There was not a significant change in oxygen SaO$_2$ during BCAA infusion, which was to be expected as all patients were in good health and had normal saturation levels (range for lowest value was 93-99%). One subject had apneas during control nights but not during BCAA infusion. Although some investigators have indicated that the hypoxic ventilatory drive is more important in sleep apnea patients than hypercapnic ventilatory drive, the results indicate enhancing the respiratory drive by BCAA infusion assists in normalizing the breathing patterns during sleep in healthy subjects.

The sleep patterns, even with the infusion of BCAAs, remained largely intact. There was no significant change in the amount of REM sleep or REM latency. The amount of stage 3 sleep and combined stage 3 & 4 sleep increased significantly during BCAA nights when compared to control night without infusion. The study demonstrates that BCAA infusions indeed affect neurophysiological functions during sleep. The accentuation of the respiratory effects of amino acids by BCAA can have important clinical relevance for patients with decreased ventilatory drive due to anesthesia, medication, prolonged administration of 5% dextrose, or sleep apneas due to different origins.

EXAMPLE NO. 2

A 31 year old, morbidly obese white female was admitted with a diagnosis of increasing shortness of breath, peripheral cyanosis secondary to morbid obesity with a history of sleep disturbance (diagnosis: sleep apnea versus obesity hypoventilation). The patient had been previously maintained on home oxygen therapy and nasal CPAP. The patient presented increasing dyspnea on exertion of a half a block, four to five pillow orthopnea, frequent night awakenings, and chronic peripheral edema. The patient also had perioral and peripheral cyanosis, complained of feeling very tired in the mornings, and had a history of lightheadedness and diffuse constant chronic numbness in the morning.

During admission, the patient's blood gases were measured. The blood gases were arterial PO2 67 mmHg, arterial PC02 50 mmHg and PH 7.34. Vital capacity was 1.1 liter (predicted 3.8), forced expiratory volume 0.81 liter (predicted 2.7).

A past medical history was taken and was significant in that a gastric stapling performed at St. Luke's eight years prior, had became "unbuttoned."

The medicines the patient was given, at the time of admission included Lasix and Aminophylline. The patient was also started on a 600 calorie diet. The patient's blood gases were: arterial PO2 46, arterial PCO2 51, PH 7.42 while awake.

The patient began a regimen of branched chain amino acid parenteral nutrition. The patient was started on a Branchamine infusion of 4%, available from Clintec Nutrition, Deerfield, Ill., at 100 ml/hr in the hospital. This was well tolerated. After the patient left the hospital, home infusions were instituted on a nightly basis at a rate of 100 ml/hr of 4% Branchamine, available from Clintec Nutrition. Soon thereafter, symptomatic improvement occurred.

Following nine months of these infusions, the patient remained stable at home, was more energetic upon awakening, and many of her morning symptoms had resolved completely. The patient's vital capacity had increased to 1.17 l and her FEV1 had increased to 0181 l/sec. Feelings of lightheadedness and other symptoms previously reported had improved as did the perioral and peripheral cyanosis the patient had experienced upon awakening.

The increase in vital capacity and FEV1 demonstrates that the Branchamine has improved the patient's sleep apnea.

EXAMPLE NO. 3

Seven chronic renal failure (CRF) patients (see Table 3 below) treated with hemodialysis three (3) times a week underwent nocturnal polysomnography and were studied on three nights prior to hemodialysis on the following day. Patients taking sedatives or antihistamines discontinued these drugs during the study period. Six of the patients were on antihypertensive medications, including betablockers.

Polysomnographic investigation revealed that only one patient had severe sleep apnea. This patent was very different from the rest both with respect to sleep and respiratory patterns and he is therefore presented separately.

The mean age of the six patients without apnea was 43 years (range 36–48 years). Their mean day weight, given as a percent of ideal body weight (the revised Metropolitan Ideal Body Weight Tables, 1985) was 91% (range 76 to 110%). Table 3 shows patient characteristics of the six non-apneic patients.

TABLE 3

| Patient Characteristics (N = 6). Mean ± SD. | | |
|---|---|---|
| | Study Patients | [normal range] |
| PH | 7.41 ± 0.08 | |
| PCO$_2$ (mm Hg) | 40.4 ± 3.0 | |
| PO$_2$ 9 mm Hg) | 93.4 ± 4.5 | |
| HCO$_3-$ (mmol/l) | 3.1 ± 5.7 | |
| Sleep pattern | | |
| Stage 1 and 2 (%) | 66 ± 12 | [63 ± 9] |
| Stage 3 and 4 % | 19 ± 9 | [12 ± 6] |
| REM sleep (5) | 14 ± 8 | [23 ± 4] |
| Sleep efficiency (%) | 70 ± 12 | [97 ± 2] |
| Sleep latency (min) | 21 ± 15 | [6 ± 4] |
| REM sleep latency (min) | 85 ± 40 | [85 ± 30] |

Normal values are based on international standards applied by sleep laboratories, matched with age and sex. Definitions are:

Sleep efficiency=total sleep time divided with total recording time; and Sleep latency=the interval between lights out and sleep onset.

REM sleep latency=the period from sleep onset to the first epoch (30 seconds of REM sleep).

No food intake was allowed after 5 p.m. on the study nights. A peripheral line (22G) was inserted in the arm contralateral to the arteria-venous dialysis access. The first night was used as a control. Accordingly, the patients did not receive any infusion the first night.

After the first night, the patients were randomized to receive either branched-chain amino acids (60 mg/kg/h =1.4 ml/kg/h, corresponding to 100 ml/h in a 70 kg person) or saline, intravenously, for 7 hours on the two (2) study nights. The maximum amount of protein infused was never greater than 35 g/patient. The BCAA solution (4% Branchamin-available from Baxter Healthcare Corporation, Deerfield, Ill.) contained 1.38 g each of isoleucine and leucine per 100 ml and 1.24 of valine per 100 ml. The infusions were started 1 hour before the patient's habitual bed-time, which was between 10.00 and 11.00 p.m. in all cases. In one patient, one of the study nights, on which branched chain amino acids were given, was repeated due to problems with venous access.

Surface electrodes and a 12 channel Grass P78 polysomnograph were used for the continuous recording of the electroencephalogram, submental electromyelogram, electro-oculogram, and electrocardiogram. Respiratory movements were monitored with pneumograph bellows around the chest and abdomen and were recorded on the polysomnograph. The pneumograph bellows were used in a semiquantitative manner to allow differentiation of obstructive and central apneas and hypopneas.

A finger oximeter (Ohmeda Biox 3700) and a capnograph (Normocap, Datex) were used to record oxyhemoglobin saturation (SaO$_2$) and ETCO$_2$. To measure ETCO$_2$ a length of thin tubing was inserted about 1 cm into the nostril of the patient and the other end was connected to the sample port of a capnograph. The capnograph was calibrated prior to each night's study. Both the oximeter and capnograph were connected to the polysomnograph for continuous recording. The presence of airflow was inferred by the ETCO$_2$ and by thermocouples at the nose and mouth.

The polysomnograms were scored for sleep stages and incidence, length, and severity of apneas/hypopneas by a registered polysomnographic technologist who was not made aware of the premise of the investigation. Following the traditional staging and scoring definitions, sleep was divided into REM (Rapid Eye Movement) sleep and non-REM sleep (Stage 1–4).

Obstructive apnea was defined as the absence of airflow in the presence of rib cage and abdominal excursions for a period of at least 10 seconds. Non-obstructive (central) apnea was defined as the absence of both airflow and respiratory movement for at least 10 seconds. Apneas with both obstructive and central characteristics ("mixed") were classified together with the obstructive apneas. Hypopnea was defined as an episode of at least 10 seconds in which the amplitude of the sum of ventilatory movement of rib cage and abdomen was less than 50% of the mean amplitude of the previous breaths. Five or more apneas per hour of sleep was considered abnormal and apnea associated with more than 5% desaturation was considered severe.

Analysis of $ETCO_2$, $SAO_2$, and respiratory and heart rate was carried out during blocks of 3-5 minutes of stable breathing (no apneas) in every sleep stage that was recorded during each hour of the sleep study. Only $CO_2$ polygraph waveforms consisting of a sharp upstroke and downstroke with a relatively flat plateau which had a slightly ascending slope were considered valid for analysis of $ETCO_2$. During each hour, the block selected for analysis was as close as possible to the middle of the hour. Thus, the measurements of breaths during each hour of sleep avoided potential bias associated with selecting breaths from only one point in time during the night of polysomnography.

The baseline consisted of a 5 minute block of stable breathing after the patient retired and before the onset of sleep. Mean values were obtained by averaging all measurements over 3 to 5 minute periods. Data from the baseline were compared to hourly measurements for midnight to 5 a.m. (this particular period was chosen since some patients did not fall asleep until midnight and many of them had to get up at 5 a.m. for early dialysis). The analyzed data from non-REM periods were for stage 1 and 2 because adequate data for stage 3 and 4 was missing in many patients (the patients had infrequent periods of REM sleep, which usually occurred at the end of the study period). Therefore, data from the last recorded REM period was used for comparison with baseline and non-REM values.

Statistical analysis was performed using Student's T-test (paired) and one-way analysis of variance (ANOVA) with the Tukey post-hoc test. A P value less than 0.05 was considered statistically significant.

Seven patients completed the three night study. Only one patient had severe sleep apnea. This patient was very different from the remaining patients both with respect to sleep and respiratory pattern, and is discussed separately. In the six patients without severe sleep apnea no significant changes in sleep quality and sleep stages, except for an increase in REM sleep, were found on the night of BCAA infusion (see Table 4 below).

TABLE 4

| Polysomnographic and respiratory data (N = 6). Mean ± SD. | | | |
|---|---|---|---|
| | Saline | BCAA | P-Value |
| Stage 1 (%) | 9 ± 19 | 6 ± 3 | NS |
| Stage 2 (%) | 56 ± 19 | 53 ± 10 | NS |
| Stage 3 and 4 (%) | 21 ± 14 | 22 ± 11 | NS |
| REM sleep (%) | 12 ± 10 | 19 ± 8 | P < 0.05 |
| Sleep efficiency (%) | 66 ± 16 | 74 ± 13 | NS |
| Sleep latency (min) | 39 ± 35 | 12 ± 10 | P = 0.1 |
| REM latency (min) | 75 ± 57 | 109 ± 80 | NS |
| Arousals (total) | 30 ± 12 | 35 ± 14 | NS |
| Arousals (>5 min) | 5 ± 3 | 5 ± 2 | NS |
| Apnea index (number/h of sleep) | 2 ± 2 | 2 ± 3 | NS |
| Apnea-Hypopnea index (number/h of sleep) | 3 ± 4 | 4 ± 5 | NS |
| Baseline $SaO_2$ (%) | 97 ± 2 | 96 ± 1 | NS |
| Lowest $SaO_2$ (%) | 90 ± 3 | 88 ± 5 | NS |

Figure 2A:
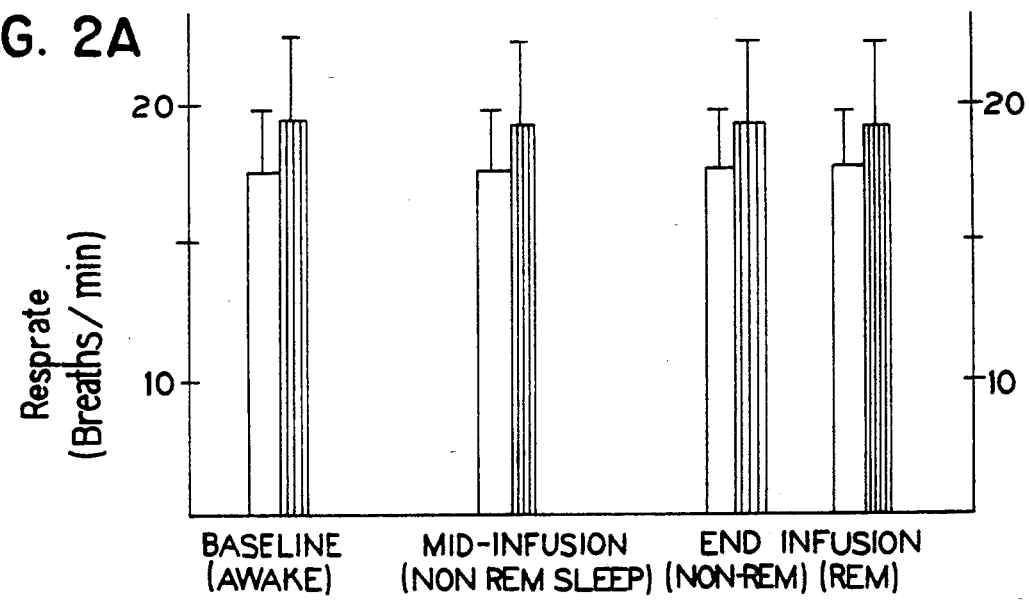
FIG. 2 illustrates, graphically, a) resprate and b) arterial oxygen saturation ($SaO_2$) during a 7 hour nocturnal infusion of saline and a 4% branched-chain amino acid solution.
Figure 2B:
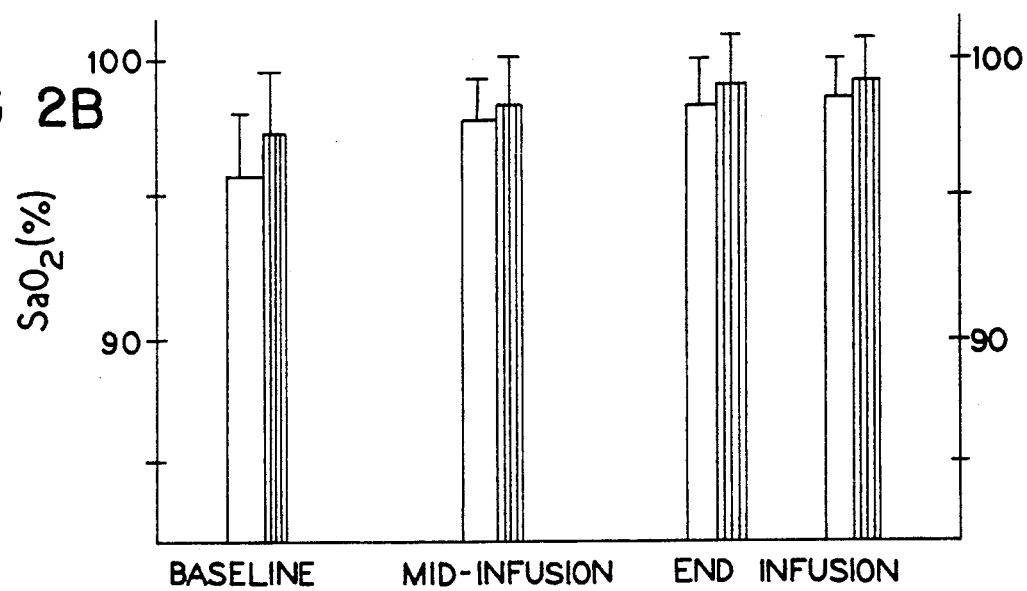

Baseline $ETCO_2$ for each night was compared with values for each hour during the night. On the placebo (saline) night no changes in $ETCO_2$ took place (see FIG. 1). As also illustrated in FIG. 1, with BCAA, however, there was a significant decrease (11%) in mean $ETCO_2$ during the 7 hour infusion both for non-REM (P<0.05) and REM sleep (P<0.05). Respiratory rate and oxygen saturation did not change significantly from baseline throughout the study nights (see FIG. 2), nor were there any significant changes in heart rate.

Patient #7 (see Table 5 below) had severe sleep apnea and also differed from the other patients in that he was overweight (150% of his ideal body weight). The patient had markedly reduced sleep efficiency on all nights (see Table 5).

Due to continuous arousals in connection with the apneas, Patient #7's sleep was scored as transitional sleep, type non-REM and REM. There was no significant increase in the ratio of REM to non-REM sleep when comparing the night of saline and BCAA, but the patient seemed to have longer arousals with BCAA (see Table 5). The BCAA night in this patient was also associated with a large decrease in the total number of obstructive apneas, corresponding to a fall in the apnea index from 85 to 31 (see Table 5). Furthermore, no central apneas occurred that night.

Because the decrease in apneas was not associated with a decrease in the number of hypopneas, the apnea-hypopnea index did not drop. However, the mean duration of both obstructive apneas and hypopneas was lower when comparing saline and BCAA (30 vs 36 seconds and 30 vs 20 seconds respectively). The change in apnea pattern was also associated with improvements in oxygen saturation (see Table 5). In addition to the difference in the lowest measured value of oxygen saturation, the time spent with oxygen saturation values less than 70% was also reduced on the BCAA night.

While the apneas during the saline night were associated with regular desaturations from a baseline of 95% down to around 40%, the majority of the apneas and hypopneas on the BCAA night only caused desaturation down to around 70%. On both nights the desaturation was worse during periods of REM sleep. Despite the improvements with BCAA, the severity of his sleep apnea made this patient a candidate for a trial of nocturnal Continuous Positive Airway Pressure (CPAP) mask and he was referred for this.

TABLE 5

| Sleep and respiratory data for Patient #7 (male, 38 years old) that had severe obstructive sleep apnea. | | | |
|---|---|---|---|
| Night | Control | Saline | BCAA |
| Sleep efficiency (%) | 57% | 55% | 47% |
| Transitional sleep* | | | |
| non REM | 76% | 62% | 57% |
| REM | 17% | 23% | 17% |
| arousals | 7% | 15% | 24% |
| Total number apnea | 363 | 323 | 94 |
| obstructive | 360 | 319 | 94 |
| central | 3 | 4 | 0 |
| Apnea index | 81 | 85 | 31 |
| Total number hypopneas | 412 | 190 | 395 |
| Apnea/hypopnea index | 173 | 135 | 160 |
| Oxygen saturation (%) | | | |
| baseline | 97 | 94 | 96 |
| lowest | 40 | 34 | 54 |

*Transitional sleep = sleep continuously interrupted by arousals.

BCAA was associated with a significant decrease in the numbers of obstructive apneas. Further, substantially less desaturation was associated with the remaining apneas and hypopneas. The oximeter used had previously been tested for accuracy down to oxygen saturation levels of 40% and found reliable within 2-3%; accordingly, the decrease in $ETCO_2$ during BCAA infusion patients can be taken as a sign of increased respiratory drive and improved alevelor ventilation.

BCAA were found to both significantly improve respiratory drive, reflected by a decrease in $ETCO_2$, and to increase the amount of REM sleep. In the one patient with severe obstructive sleep apnea, BCAA reduced both the total number of apneas and the severity of desaturation in the remaining apneas and hypopneas.

The results indicate that BCAA may be of use in the treatment of sleep apnea in chronic renal failure patients. It is further noted that BCAA can be given without worsening the already disturbed sleep pattern in these patients.

Although the BCAA can be given both parenterally and enterally, in chronic renal patients, it may be desirable to give the BCAA intradialytic. This eliminates both practical problems of administration and eliminates the risk of fluid overloading.

In continuous ambulatory peritoneal dialysis patients, the BCAA can be given through the peritoneal. In such a case, preferably a maximum of 100 gms of BCAA should be administered.

Data are presented as mean±SD. Normal values are based on international standards applied by sleep laboratories, matched with age and sex. Definitions are: sleep efficiency=total sleep time divided with total recording time; sleep latency=the interval between lights out and sleep onset.

EXAMPLE NO. 4

In this example, the inventors examined in a double-blind randomized fashion, whether intradialytic BCAA (3 times per week for one month) can improve patients' sleep as compared to control.

Six patient with chronic renal failure (CRF) on hemodialysis were studied in a randomized and double blind crossover study.

At baseline, patients were evaluated by a complete medical history, together with a physical examination. Dry weight was recorded. Blood samples were drawn in accordance with a clinical care plan, and for plasma amino acid profile. Urea kinetic modelling principles were performed to assess the adequacy of dialysis by determining Kt/V, and nutritional status of the patients was assessed by PCR.

The subjects filled out a questionnaire to evaluate sleep disturbances and daytime mental mood and sleepiness scoring. Before starting the BCAA/placebo supplementation, the subjects underwent a one night study in the Sleep-Awake Disorder Center of Montefiore Hospital to evaluate their sleep pattern and incidence of respiratory disturbances during sleep.

After baseline assessments, patients were randomly assigned to receive 1000 ml of a 4% BCAA solution of 100% BCAA (Branchamin 4%, Travenol Laboratories, Deerfield, Ill.) or 1000 ml of placebo solution (normal saline) during each dialysis session for three times a week for one month. Those patients given BCAA for the first month, received the placebo infusion and those on placebo infusion were given the BCAA solution for another month. After the end of the second month, assessments were again repeated.

The sleep study was carried out on the night immediately following hemodialysis. During the study period, the subject's nephrologist would change and monitor the patient's need for medication, including medication which affects sleep pattern (hypnotics, sedative, antihistamines). The patients were asked to fill out a questionnaire daily regarding their need for medication and self-assessment of headache, fatigue, and appetite.

During the night spent in the sleep study center, surface electrodes and a 12 channel Grass P78 polysomnograph (PSG) were employed for continuous recording of the electroencephalogram, submental electromyelogram, electro-oculogram, and electrocardiogram. Respiratory movements were monitored with pneumograph bellows around the chest and abdomen and recorded on the PSG. The pneumograph bellows was used in a semiquantitative fashion to allow differentiation of obstructive and central apneas and hypopneas.

The finger oximeter (Ohmeda Biox 3700, Ohmeda, Louisville, Colo., U.S.A.) with an accuracy of ±1.5% and a capnograph (Normocap, Datex, Helsinki, Finland) with an accuracy of ±2% was used to record oxyhemoglobin saturation ($SaO_2$) and $ETCO_2$. To measure $ETCO_2$, a length of thin tubing was inserted about 1 cm into the nostril and the other end connected to the sample port of a capnograph. The capnograph was calibrated prior to each night's study. Both the oximeter and capnograph were connected to the PSG for continuous recording. The presence of airflow was inferred by the $ETCO_2$ and by thermocouples at the nose and mouth.

The polysomnograms were scored for sleep stages and incidence, length, and severity of apneas/hypopneas by a registered polysomnographic technologist unfamiliar with the premises of the study. Following the traditional staging and scoring definitions, sleep was divided into REM (Rapid Eye Movement) sleep and non-REM sleep (Stage 1-4).

Analysis of $ETCO_2$, $SaO_2$, and respiratory and heart rate was carried out during blocks of 3-5 minutes of stable breathing (no apneas) in every sleep stage that is recorded during each hour of the sleep study. Only $CO_2$ polygraph waveforms consisting of a sharp upstroke and downstroke with a relatively flat plateau which has a slightly ascending slope were considered valid for analysis of $ETCO_2$. During each hour, the block selected for analysis was as close as possible to the middle of the hour. Thus, the measurements of breaths during each hour of sleep will avoid potential bias associated with selecting breaths from only one point in time during the night of polysomnography. The baseline consisted of a 5 minute block of stable breathing after the patient has retired and before onset of sleep.

Mean values were obtained by averaging all measurements over the 3-5 minute periods. Data from baseline were compared to hourly measurements from midnight to 5 a.m.

Differences between experimental (BCAA-supplementation during the dialysis) and control (placebo supplementation during the dialysis) values were compared as paired variables using the paired t-test. A P-value of less than 0.05 was considered statistically significant.

The results of the study are set forth below in Table 6:

TABLE 6

| INTRADIALYTIC BCAA-INFUSION IN PATIENTS WITH SLEEP DISORDERS (mean ± sd, range in parenthesis) | | | |
|---|---|---|---|
| | baseline | saline | BCAA |
| Subjective nightly sleep (h) | 4.3 (2.5–8) | 3.5 (3.25–3.75) | 6.25 (4.25–7.5) |
| Sleep efficiency (%) | 56 ± 24.8 | 74.3 ± 75.5 | 37.2 ± 30.4 |
| Sleep latency (min) | 45± 21 (21.5–79) | 74.3 ± 75.5 (12–213) | 37.2 ± 30.4 (13.5–84.5) |

TABLE 6-continued

INTRADIALYTIC BCAA-INFUSION IN PATIENTS
WITH SLEEP DISORDERS (mean ± sd, range in parenthesis)

|  | baseline | saline | BCAA |
|---|---|---|---|
| Sleep stage 1 (%) | 14.9 ± 15.5 | 9 ± 10.6 | 4 ± 2 |
| (4.17 ± 1.65) | (5–45.7) | (2.8–30.2) | (2.3–7.7) |
| Sleep stage 2 (%) | 51.6 ± 10.6 | 49.3 ± 20.4 | 51.2 ± 24.2 |
| (53.8 ± 7.7) | | | |
| Sleep stages 3 & 4 (%) | 15 ± 17.3 | 14.1 ± 11 | 26.6 ± 27.6 |
| (14 ± 7.3) | | | |
| REM sleep (%) | 6.8 ± 8 | 13.8 ± 10.4 | 16.6 ± 8.2 |
| (26.2 ± 5.3) | (0–19.4) | (0–30) | (5.7–26.9) |
| Apnea-total | 42.3 ± 53 | 48.8 ± 52 | 45.8 ± 61.4 |
| Apnea - index | 12.1 ± 14.3 | 12.7 ± 13.3 | 11.3 ± 16.5 |
| Arousals | 18.8 ± 10.7 | 17 ± 8.8 | 21.5 ± 9.3 |
| Arousals > 5 min | 5.2 ± 1.8 | 2.8 ± 2.7 | 3.7 ± 2.5 |
| SaO$_2$-baseline (%)/lowest (%) | 96/78 | 96/76 | 95/79 |
| Hypopnea | 32.7 ± 38 | 39.2 ± 51 | 21.2 ± 17.6 |
| Apnea-hypopnea-index | 20.9 ± 23.9 | 22.7 ± 23.7 | 16.2 ± 18.9 |

During treatment, there was a significant ($p<0.05$) improvement in every patients' sleeping time (from 4.3 to 6.2 hours/night) based on daily subjective recordings.

In 2 of 6 patients, REM sleep increased from 0% to 27% and 17%, respectively. Normal REM sleep is 26%. Total sleeping time increased by 33% and 56%, respectively. In other patients, there was marked variation between saline and BCAA treatments.

It was also found that deeper non-REM stages 3 and 4 increased in means from 15% to 27% (normal is greater than 15%).

Additionally, at baseline, 4 of 6 patients with marked apnea (greater than 5 apneas/hour), 2 improved with BCAA (from 19 to 1 and from 11 to 8 apneas/hour).

As evidenced above, intradialytic infusion of BCAA improves the subjective quality of sleep in patients with renal failure. In one third of patients there also is a positive effect seen in sleep laboratory assessment on the second night after BCAA infusion.

It should be understood that various changes and modifications to the presently preferred embodiments described herein will be apparent to those skilled in the art. Such changes and modifications can be made without departing from the spirit and scope of the present invention and without diminishing its attendant advantages. It is therefore intended that such changes and modifications be covered by the appended claims.

I claim:

1. A method for increasing the REM stage of sleep and duration of sleep in a patient requiring same comprising the step of:
   administering to a patient a therapeutically effective amount of an amino acid solution including at least approximately 60% branched-chain amino acids.

2. The method of claim 1 wherein the solution is administered parenterally.

3. The method of claim 1 wherein the solution is administered enterally.

4. The method of claim 1 wherein approximately 4 grams of branched-chain amino acids are administered per hour.

5. The method of claim 1 wherein the solution is administered intradialytic.

6. The method of claim 1 wherein the amino acid solution includes Isoleucine, Leucine, and Valine.

7. A method for increasing the REM stage of sleep and duration of sleep in a patient requiring same comprising the step of:
   administering to a patient a therapeutically effective solution including approximately 60 to about 85% branched-chain amino acids.

8. The method of claim 7 wherein the solution is administered parenterally.

9. The method of claim 7 wherein the solution is administered enterally.

10. The method of claim 7 wherein approximately 0.443 grams of total nitrogen are administered per hour.

11. The method of claim 7 wherein approximately 4 grams of branched-chain amino acids are administered per hour.

12. The method of claim 7 wherein the solution is administered intradialytic.

13. A method for increasing the REM stage of sleep and duration of sleep in a chronic renal failure patient undergoing dialysis comprising the step of:
   administering during dialysis, intradialytic, to a chronic renal failure patient a therapeutically effective amount of an amino acid solution including at least approximately 60% branched-chain amino acids in a dialysis solution.

14. The method of claim 13 wherein the solution includes Isoleucine, Leucine, and Valine.

15. The method of claim 13 wherein the patient is undergoing hemodialysis.

16. A method for increasing the REM stage of sleep and duration of sleep in a chronic renal failure patient undergoing dialysis comprising the step of:
   administering to a patient during dialysis, intradialytic, a therapeutically effective solution comprising approximately 60 to about 85% branched-chain amino acids.

17. The method of claim 16 wherein the solution includes Isoleucine, Leucine, and Valine.

* * * * *